(12) United States Patent
Viebach et al.

(10) Patent No.: US 7,371,209 B2
(45) Date of Patent: May 13, 2008

(54) ENDOSCOPE HEAD

(75) Inventors: Thomas Viebach, Pischertshofen (DE); Fritz Pauker, Friedberg (DE)

(73) Assignee: STM Medizintechnik Starnberg GmbH, Weinheim (DE)

( * ) Notice: Subject to any disclaimer, the term of this patent is extended or adjusted under 35 U.S.C. 154(b) by 279 days.

(21) Appl. No.: 10/718,238

(22) Filed: Nov. 19, 2003

(65) Prior Publication Data
US 2004/0147807 A1 Jul. 29, 2004

(30) Foreign Application Priority Data
Nov. 22, 2002 (DE) ................................ 102 54 609

(51) Int. Cl.
*A61B 1/00* (2006.01)
(52) U.S. Cl. ................ 600/102; 600/112; 600/129; 600/132; 600/172; 600/173; 600/174; 600/175
(58) Field of Classification Search ............... 600/101, 600/102, 104, 109, 127, 129, 131, 132, 117, 600/118
See application file for complete search history.

(56) References Cited

U.S. PATENT DOCUMENTS 5,398,670 A * 3/1995 Ortiz et al. ................. 600/114
5,438,975 A * 8/1995 Miyagi et al. .............. 600/109
5,518,501 A * 5/1996 Oneda et al. ............... 600/127
5,643,175 A 7/1997 Adair
6,095,970 A * 8/2000 Hidaka et al. .............. 600/110
6,447,445 B1 9/2002 Hirano

FOREIGN PATENT DOCUMENTS

WO    WO 02/056756 A2    7/2002

\* cited by examiner

*Primary Examiner*—Linda C. M. Dvorak
*Assistant Examiner*—Matthew J. Kasztejna
(74) *Attorney, Agent, or Firm*—Hanley, Flight & Zimmerman, LLC

(57) ABSTRACT

The invention relates to an endoscope head which is equipped with a plurality of function-related units such as an optical/lens system, illuminating elements, rinsing nozzles and the like. The endoscope head substantially comprises a plurality of modular plug-in or click-in function-related supports for receiving and/or forming the function-related units.

12 Claims, 5 Drawing Sheets

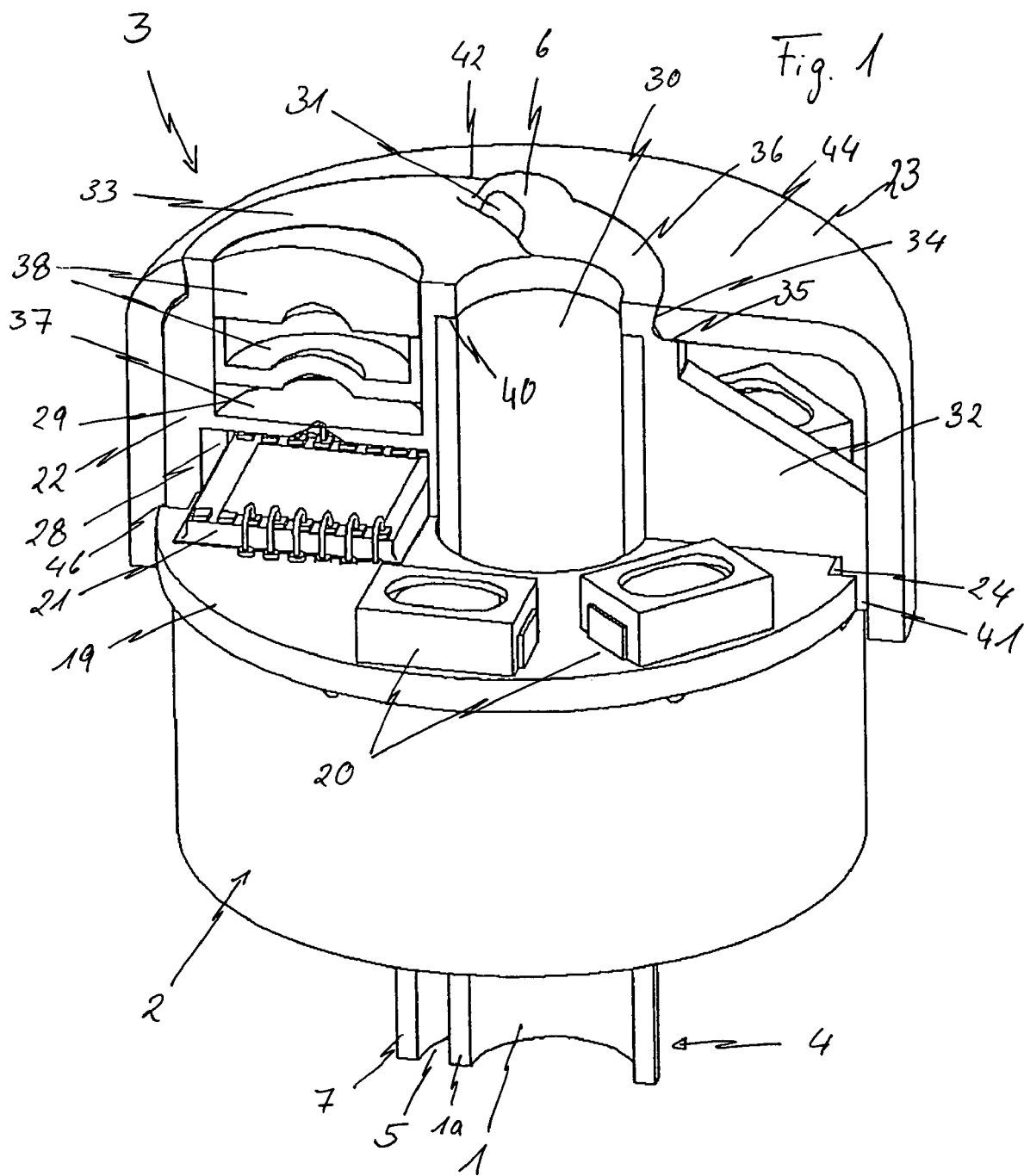

ENDOSCOPE HEAD

BACKGROUND OF THE INVENTION

The invention generally relates to an endoscope head comprising a plurality of function-related units or elements.

Endoscopes are especially used in medicine for the diagnostic viewing (mirror examination) of body cavities and hollow organs. Flexible endoscopes having a working passage for introducing instruments and an endoscope head which can be equipped with illuminating means, image transmitting means and other devices are sufficiently known from the prior art.

However, it has also been known since these endoscopes were introduced that by virtue of the inexpert cleaning, disinfection and sterilization thereof when the endoscopes are utilized several times, microorganisms, for instance, can be transmitted which, in turn, can transmit diseases from one patient to the other. Sufficient disinfection and sterilization of the endoscope involves considerable work and cost efforts and/or there also seem to be pathogens which are particularly resistant to the conventional disinfection methods.

Therefore, in principle, endoscopes are provided with endoscope heads consisting of a plurality of electrical, optical and hydraulic function-related units or elements which are placed onto a support and then are cast-in with a body-tolerated material such as silicone, for instance. This operation is carried out in such a manner that at the same time the distal end of the endoscope shaft on which the head is mounted is also cast-in so as to seal the transition between the endoscope head and the endoscope shaft.

It has turned out that the conventional manufacturing mode of such an endoscope is very expensive especially due to the structure of the endoscope head and therefore endoscopes which can repeatedly be used are efficient. These have the drawback, however, that they always have to be disinfected in a costly manner.

SUMMARY OF THE INVENTION

In order to avoid the above-mentioned difficulties, risks and related costs, it is an object of the invention to provide an endoscope, especially a head for an endoscope, which can be manufactured in such a simple and inexpensive manner that it can be disposed of after use.

This object is achieved by the invention which generally comprises an endoscope head which is made up of a number of modular function-related supports for receiving and/or forming appropriately allocated function-related units which the endoscope has to include in accordance with its provided purpose of use. Prior to mounting, the function-related supports are equipped with the respective function-related units or elements and are subsequently assembled, preferably by snap-on or clamping connections.

Preferably for mounting the head onto an endoscope shaft a kind of intermediary or mounting adapter is provided which produces and ensures, respectively, a connection between the function-related elements of the head and the corresponding lines or conduits in the endoscope shaft.

By virtue of the modular structure of the head, the individual modular parts can be manufactured and the head can be mounted in a very inexpensive way. Hence, by reducing the manufacturing costs of the head, it is possible to provide an endoscope which can be a single-use endoscope.

Further advantageous embodiments of the invention will become more apparent from the following description of the preferred embodiment and from the appended claims. It is to be understood that the foregoing general description and the following detailed description are exemplary and provided for purposes of explanation only, and are not restrictive of the invention, as claimed.

BRIEF DESCRIPTION OF THE DRAWINGS

Hereinafter the invention will be described in detail by way of preferred embodiments with reference to the enclosed schematic figures, in which:

FIG. 1 shows an isometric partial section of an endoscope shaft according to the invention seen obliquely from the top;

DETAILED DESCRIPTION OF THE PREFERRED EMBODIMENTS

Figure 2A:
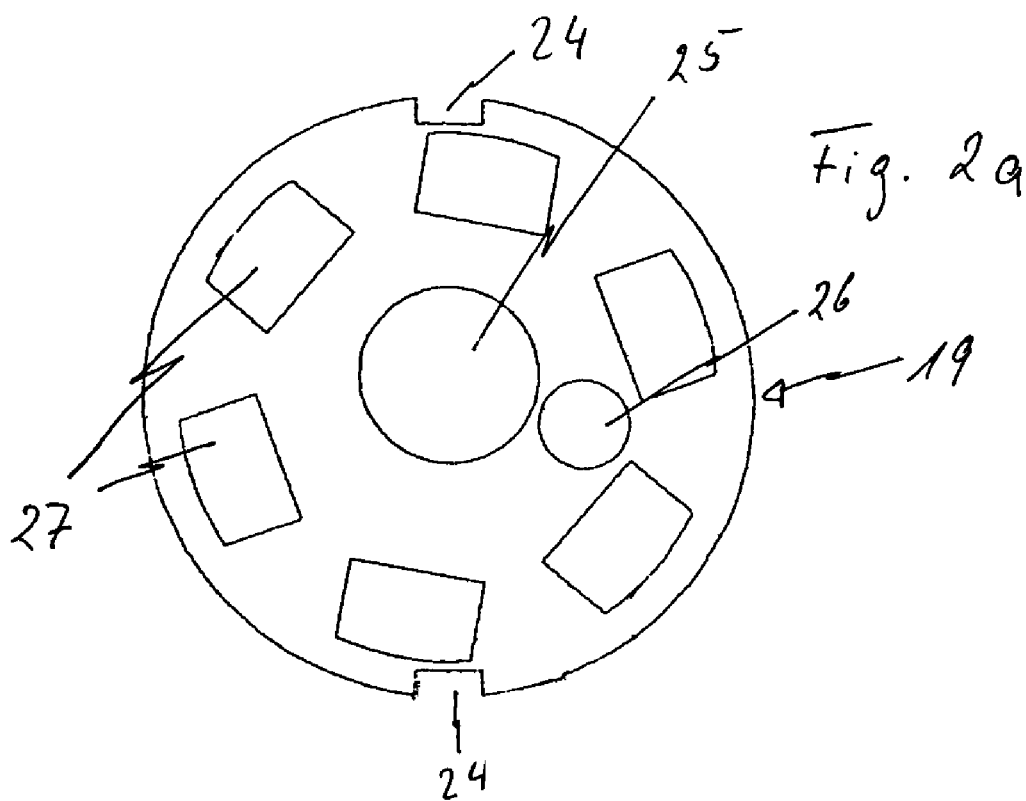
FIG. 2a and/or 2b shows a lower side and/or upper side of a support member for electric components pertaining to the endoscope head according to FIG. 1.
Figure 2B:
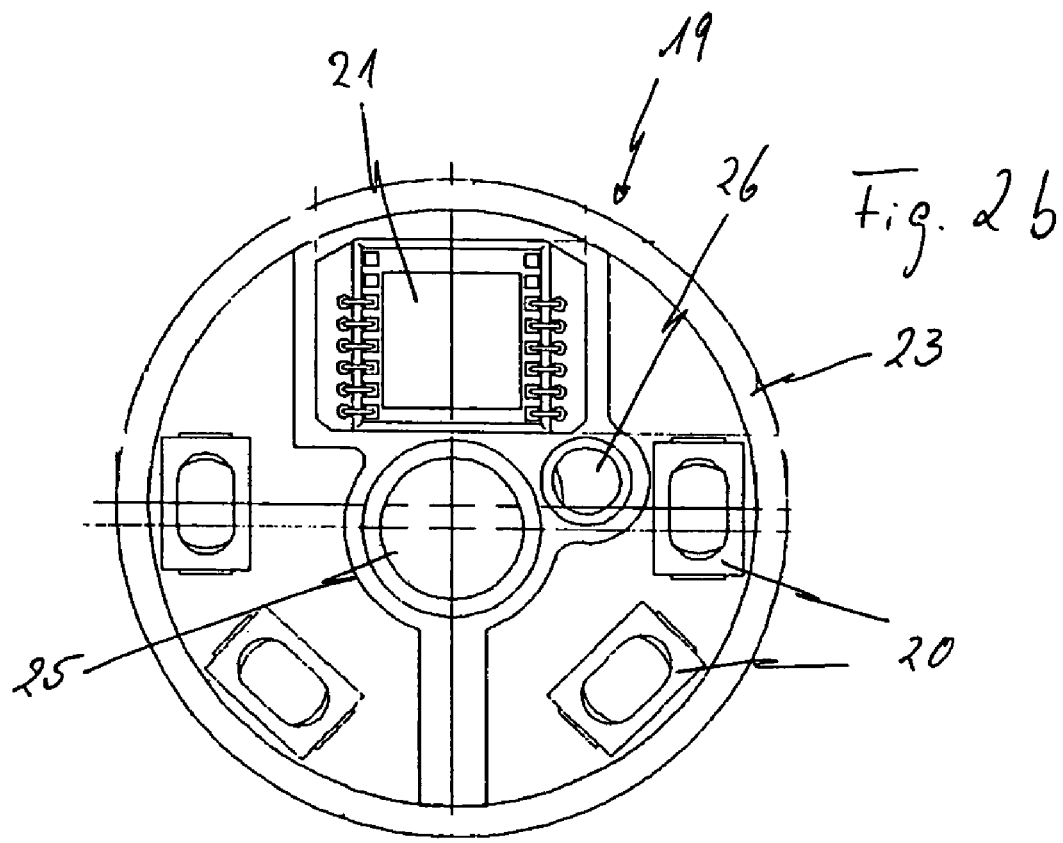

By way of FIGS. 1 to 4 an endoscope including an endoscope head according to an embodiment of the invention is described.

The endoscope substantially consists of a (not represented) flexible endoscope shaft or tube which receives a centrally extending working passage or conduit 1, a mounting adapter 2 fixed to the one distal end of the endoscope tube and an endoscope head 3 which is attached to the endoscope tube via the mounting adapter 2. The endoscope head 3 according to the invention in turn substantially consists of a number of modular function-related supports 19, 22, 23 for receiving and/or forming appropriately allocated particular function-related units 20, 21, 38 required by the endoscope head for carrying out, for instance, an examination of a human body cavity.

The function-related supports provided in this preferred embodiment are:

a support member 19 for receiving electronic components 20, 21;

a retaining/holding element 22 for receiving/forming an optical/lens system; and a protection cap 23 for covering the two aforementioned function-related supports.

The endoscope tube is interesting to the invention described here in so far as the mounting adapter 2 is quasi designed as an intermediary for receiving and linking, respectively, particular elements of the endoscope tube with the endoscope head. For instance, the endoscope tube includes (not represented) bending elements for bending its distal end portion, (likewise not represented) electrically or light conductive cables or lines which supply power to the electronic components 20, 21 in the endoscope head 3 and by which information can be transmitted, and a double conduit 4 consisting of an internal working passage 1 for introducing instruments into the cavity to be viewed and of an external rinsing conduit 5 for supplying a rinsing nozzle 6 disposed at the endoscope head 3 with wash, the nozzle constituting a further function-related unit.

The passage arrangement is shown as having two cylindrical passage elements or pipes 1a, 7 having different outside diameters, wherein the smaller conduit member 1a is located in the larger conduit member 7 in such a way that the conduit walls thereof are tangent to each other at a longitudinal side, i.e. they are arranged coaxially but axially displaced with respect to each other. Thus the working passage 1 is formed by the inner conduit member 1*a*, and the rinsing conduit 5—in this case sickle-shaped—is formed by the area between the outer conduit member 7 and the inner conduit member 1*a*. By virtue of this arrangement the two conduit members 1*a*, 7 have different longitudinal axes which are displaced by the difference of their radii (referred to as axial displacement in the following). As regards the length, the inner conduit member 1*a* is longer than the outer conduit member 7 by an amount defined by the height of the endoscope head. Thus the double conduit 4 is continued merely by the working passage 1 from a particular point.

Figure 3:
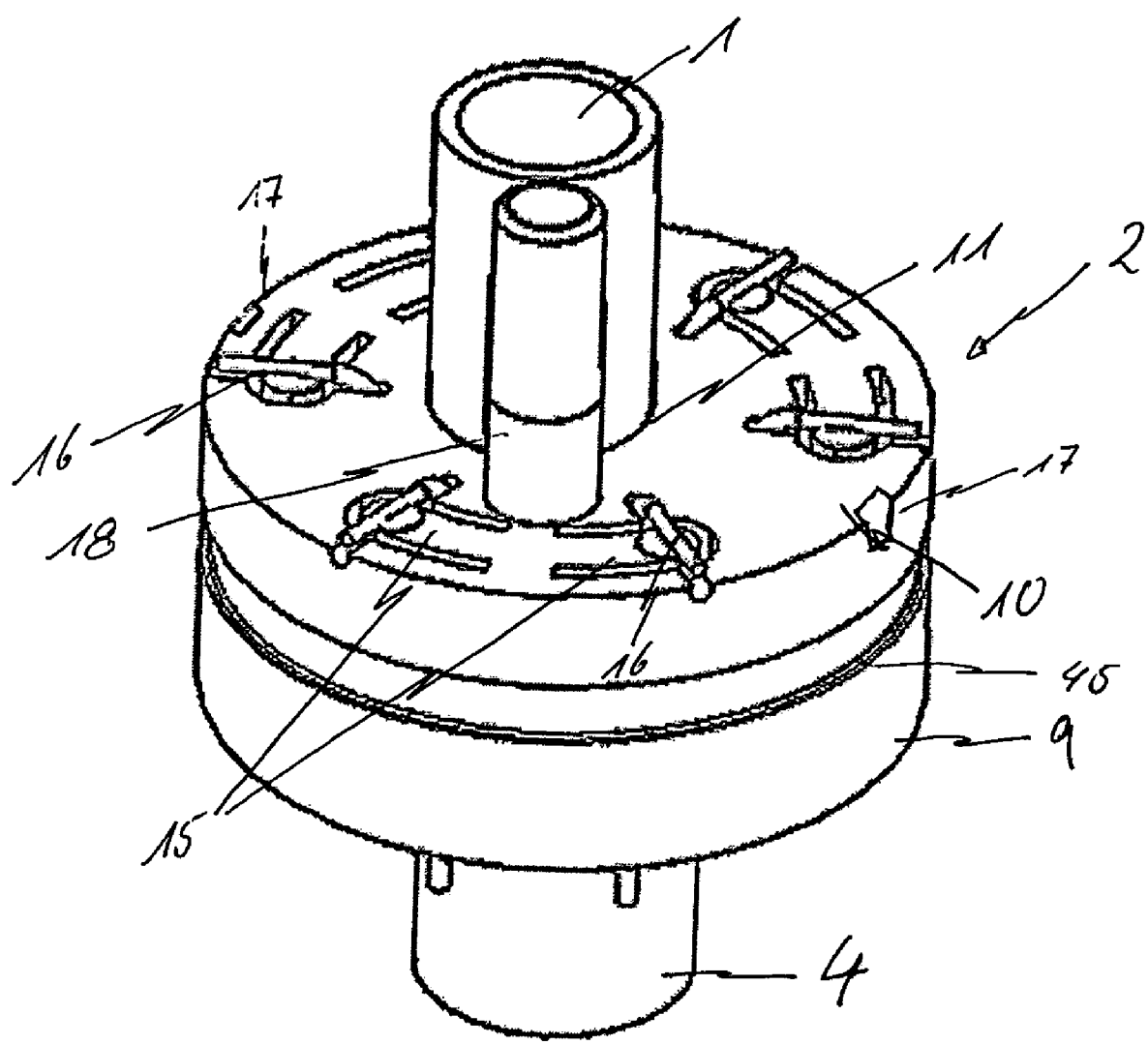
FIG. 3 shows a perspective view of the upper side of a mounting adapter according to the invention.
Figure 4:
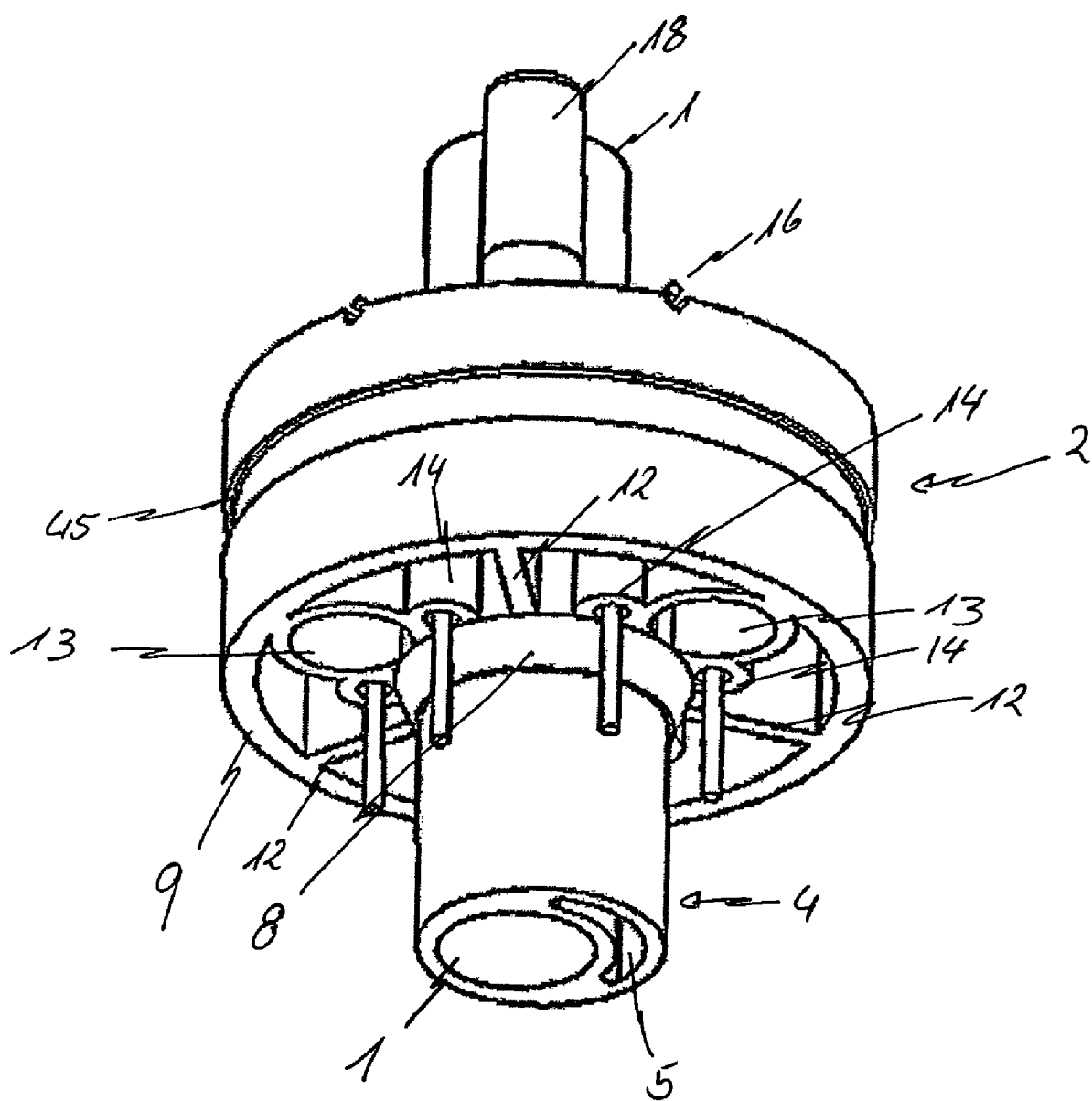
FIG. 4 shows a perspective view of the lower side of the mounting adapter according to the invention of FIG. 3

The mounting adapter 2 according to FIGS. 3 and 4 substantially consists of two concentric coincident cylinder elements 8, 9 having different radii which are interconnected via an adapter plate 10 which is normal to the cylinder axis and which is formed preferably integrally with the former on a front side of both cylinder elements 8, 9. The outer cylinder element 9 has an outside diameter substantially corresponding to the outside diameter of the endoscope tube and the inside diameter of the inner cylinder element 8 substantially corresponds to the outside diameter of the double conduit 4. A circular hole 11 in the adapter plate 10, however, has an inside diameter corresponding to the outside diameter of the working passage 1 and its center point is displaced by the displacement of the conduit elements with respect to the center of the cylinder elements 8, 9. Thus, in the transition between the inner cylinder element 8 and the adapter plate 10, a sickle-shaped projection is formed which serves as a support of the mounting adapter 2 on the double conduit 4.

The cavity in the form of a circle segment between the cylinder elements 8, 9 is divided into three sections by radial ribs 12 and in the middle of each section there is provided a cylindrical receiving means 13 for receiving the bending elements; this receiving means extends axially and its wall is in contact both with the inner 8 and with the outer 9 concentric cylinder elements of the adapter 2. Two cylindrical cable conduits 14 are arranged on both sides of the receiving means 13, likewise extend axially and their wall is in contact both with the inner cylinder element 8 and with the receiving means 13.

In the area in which the cable conduits 14 abut against the adapter plate 10, tangentially extending contact arms 15 which are resilient in the axial direction are formed in the adapter plate 10 within the thickness of the latter; cables passing through the cable conduits 14 are connectable to the lower sides of the contact arms 15, and the upper sides of the latter are provided with contact points (pads) 16 projecting from the surface of the adapter plate 10.

Moreover, at the outer edge of the mounting plate 10, two opposite notches 17 are provided, which notch both the adapter plate 10 at its edge and the outer cylinder element 9 and which are radially opposed. Furthermore, an annular recess 45 is provided at the outer edge of the outer cylinder 9.

The mounting adapter 2 has, at its mounting plate 10, a rinsing pipe 18 which extends in parallel thereto. In the area of the working passage 1 without rinsing conduit, when the mounting adapter 2 is installed, especially by being pushed onto the endoscope tube, rinsing pipe 18 is connected to the rinsing conduit 5 via an opening in the adapter plate 10.

By the above-described ratio between the inside diameter of the inner cylinder element 8 and the inside diameter of the circular hole 11 of the adapter plate to the respective diameters of the working passage 1 and the double conduit 4, respectively, the mounting adapter 2 can be easily installed, especially by being pushed onto the working passage 1, wherein the projection, sickle-shaped at the transition between the adapter plate 10 and the inner cylinder element 8, is supported on a transition between the working passage with rinsing conduit (double conduit) 4 and without rinsing conduit 1, wherein the cables can be connected by the cable conduits 14 to the contact points 16 and the bending elements of the endoscope tube can be connected to the receiving means 13.

In this context it is pointed out that in the foregoing description reference has partly been made to the endoscope head according to this embodiment, wherein the mounting adapter according to the invention can also be used for other already existing endoscope heads for mounting them to an endoscope shaft.

Hereinafter the endoscope head according to the invention is described in detail especially by way of FIGS. 1-4.

The support member 19 has a plate shape substantially corresponding to the shape of the mounting plate 10, i.e. the axis of the outer edge and the axis of the inner circular hole 25 of the support member 19 are again displaced with respect to each other by the displacement of the two conduit members 1, 7. Moreover the support plate of support member 19 has two notches 24 at its outer edge and an eccentric rinsing tube hole 26 is worked through the support member 19 through which the rinsing tube 18 can be passed. When the support member 19 is supported on the mounting plate 10 and the rinsing tube 18 is passed through the eccentric rinsing tube hole 26 of the support member 19, the notches 24 in the support plate and the notches 17 in the mounting plate as well as the circular hole 11 of the mounting plate and the circular hole 25 of the support plate are respectively flush with each other.

Six contact fields 27 are arranged at a regular distance on the lower side of the support member 19, and are in contact with the contact points 16 of the mounting plate 10 when the support member 19 is supported on the mounting plate 10 and the notches 17, 24 are flush with each other. The contact fields 27 provide an electric contact between the lower side and the upper side of the support plate 19. At the upper side of the support plate there are arranged four illuminating members 20 each of which is connected to one of the contact fields 27 and an optical sensor chip 21 is in contact with a further contact field 27 of the support member which is provided in the vicinity of either of the two notches 24. If a line is drawn between the centers of the opposite notches 24, the line halves both the support plate 19 and the optical sensor chip 21 and two illuminating members 20 at a time are arranged symmetrically with respect to this line.

The retaining/holding element for the optical/lens system 22 substantially consists of a cubical sensor chip chamber 28, a cylindrical lens chamber 29 arranged on top and being separated from the sensor or camera chip chamber 28 by a partition, a cylindrical working passage 30 extending in the axial direction next to the two chambers and a cylindrical rinsing tube passage 31 extending in parallel thereto. Moreover, a slanted reinforcing rib 32 is arranged at the side of the working passage 30. The superimposed chambers 28, 29, the working passage 30 and the rib 32 are symmetrical with respect to a common plane which is normal to the support member 19 and halves the supporting member 19. The rinsing tube passage 31 is arranged outside this plane. As one can furthermore take from FIG. 1, the retaining/holding element 22 is formed in one piece.

Up to a certain height, the retaining/holding element 22 has an outer contour corresponding to the shapes of the pertinent chambers 28, 29 and passages 30, 31 enveloping these shapes. From a certain height the outer contour changes into the shape of a round disk 33 which has a setoff 34 at its upper end. Thus, two superimposed concentric and round disk sections 35, 36 are formed here, wherein the upper disk section 36 opens slightly conically to the top. A section across this setoff 34 substantially results in an L shape whose upright leg is a bit inclined so that a slightly acute angle is formed between the legs. The height of the setoff 34 substantially corresponds to the thickness of a protection cap 23 described later.

The sensor chip chamber 28 is open to the bottom and has such dimensions that it can receive and/or enclose the sensor chip 21. The cylindrical lens chamber 29 is arranged on top thereof, and both chambers are separated from each other by a wall 37 having a central hole. The lens chamber 29 accommodates at least one optical lens 38 and/or an optical/lens system which can optionally be adapted to be zoomed and is either directly fixed to lens supports or can be inserted into the chamber in the form of a prefabricated cartridge. The lens chamber 29 is open to the top, however it is preferably covered by a translucent cover 39.

Up to a predetermined height, the working passage 30 has an inside diameter corresponding to the outside diameter of the working passage 1 without rinsing conduit. At its end, a setoff 40 is provided whose offset depth corresponds to the thickness of the working passage 1 in the area without rinsing conduit.

The rinsing passage 31 has an inside diameter which substantially corresponds to the outside diameter of the rinsing pipe 18 and ends at the upper end of the lens retaining/holding element 22 in the nozzle 6 directed to the cover of the lens chamber 29.

Moreover, the retaining/holding element 22 for the optical/lens system has, at the outer lower side of the rib 32 and at the opposite side thereto adjacent to the sensor chip chamber 28, a clamping projection 41 which is adapted to engage with one notch of the support plate 24 at a time and, thus, a fixed mechanical connection can be produced therebetween. The distance between the center between the clamps 41 and the axis of the working passage 30 in turn corresponds to the displacement of the two conduit members 1, 7.

The protection cap 23 substantially has the shape of an upside-down cup or mug. The inside diameter thereof corresponds to the outside diameter of the support member 19 and its "cup bottom" 44 has a round opening 42 whose diameter corresponds to the diameter of the upper slightly conical disk 36 of the lens retaining/holding element 22 at half height. The inner edge of the opening 42 in the "cup bottom" 44 is rounded and the protection cap 23 consists at least partially of a translucent material and altogether has more strength than the material of the retaining/holding element 22 for the optical/lens system. Furthermore the protection cap 23 has provided an annular projection 46 at its inner wall.

Now the assembly of the endoscope head 3 will be described.

The support member 19 is equipped with the illuminating members 20 and the optical sensor chip 21, as described in the foregoing. Then the retaining/holding element 22 supporting the optical lens 38 is put onto the support plate 19, wherein the clamping projections 41 of the lens retaining/holding element engage the notches 24 in the support plate and a mechanical connection is brought about therebetween. The retaining/holding element 22 for the optical/lens system is now arranged in such a manner that the optical sensor chip 21 is covered by the sensor chip chamber 28 and light from outside can be incident on the optical sensor chip through the lens chamber cover 39, the lens 38 and the hole in the partition 37. At the same time the inner surface of the working passage 30 is flush with the inner surface of the inner hole 25 in the support member 19 and the inner surface of the rinsing tube duct 31 is flush with the inner surface of the eccentric rinsing tube hole 26 in the support member 19. The illuminating members 20 on the support plate 19 are not impaired by the installation, especially accomplished by pushing on retaining/holding element 22.

Now the protection cap or sheathing 23 can be attached to the assembled arrangement of the support member 19 and the lens retaining/holding element 22. The arrangement is introduced to the cup-shaped protection cap 23 with the lens retaining/holding element 22 ahead, wherein the upper slightly conical disk section 36 is aligned with the opening 42 in the "cup bottom" 44 and the inner wall of the protective sheathing is aligned with the circumference of the support member 19. By virtue of the conical shape of the upper disk section 36, the rounding of the edge of the opening in the "cup bottom" 44 of the protective sheathing 23 and the fact that the lens retaining/holding element 22 is made of a softer material than the protective sheathing 23, the protective sheathing 23 can be pressed to the lens element 22, whereby a mechanical connection is formed between the conical disk section 36 and the opening 42 of the protective sheathing 23, said connection holding the protective sheathing 23 together with the lens retaining/holding element 22 and the support plate 19 attached thereto. Thus, an assembled endoscope head 3 has been formed, which can now be connected to the endoscope tube via the mounting adapter 2, as this will be described hereinafter.

As already mentioned, the mounting adapter 2 is connected to the endoscope head 3, wherein the area of the working passage or conduit 1 without rinsing conduit projects from the mounting adapter 2. The assembled endoscope head 3 can now be installed, especially by being pushed onto the mounting adapter 2 by introducing the working passage 1 without rinsing conduit through the circular hole 25 of the retaining/holding element 22 into the working passage 30, wherein at the same time the rinsing tube 18 of the adapter 2 is inserted through the rinsing tube hole 26 of the support plate 19 into the rinsing tube guide 31, and the clamping projections 41 of the lens retaining/holding element 22 are introduced into the notches 17 of the mounting member 2. The length of the working passage 1 projecting from the mounting adapter 2 is selected such that its end is adjacent to the recess 40 of the working passage 30 in the assembled state. The projection 46 of the protective sheathing 23 applied to the mounting adapter 2 engages with the annular recess 45 of the mounting adapter 2, and thus constitutes a mechanical connection between the endoscope head 3 and the mounting adapter 2.

In the arrangement assembled in this way of combining the endoscope head 3 and the mounting adapter 2, the contact surfaces 27 of the support plate 19 are now in safe contact with the contact points of the mounting adapter 2, because the lower surface of the support plate 19 is supported on the surface of the mounting adapter 2 flush with the same and thus the resilient contact point arms 15 are pressed a bit downward, as the contact points 16 project slightly from the surface of the mounting adapter 2. Thus the contact points 16 are biased in the assembled state so-to-speak against the contact surfaces 27.

In this way, an endoscope can be manufactured, wherein the function-related supports used in building up the endoscope head, i.e. the support plate 19, the lens retaining/holding element 22 and the protective sheathing 23, can be manufactured separately from each other, then can be assembled after being equipped with the selected function-related units to form the endoscope head 3, and finally the endoscope head 3 can simply be fixed above the mounting adapter 2 onto the endoscope tube.

Hereinafter modifications of the invention will be described.

Figure 5:
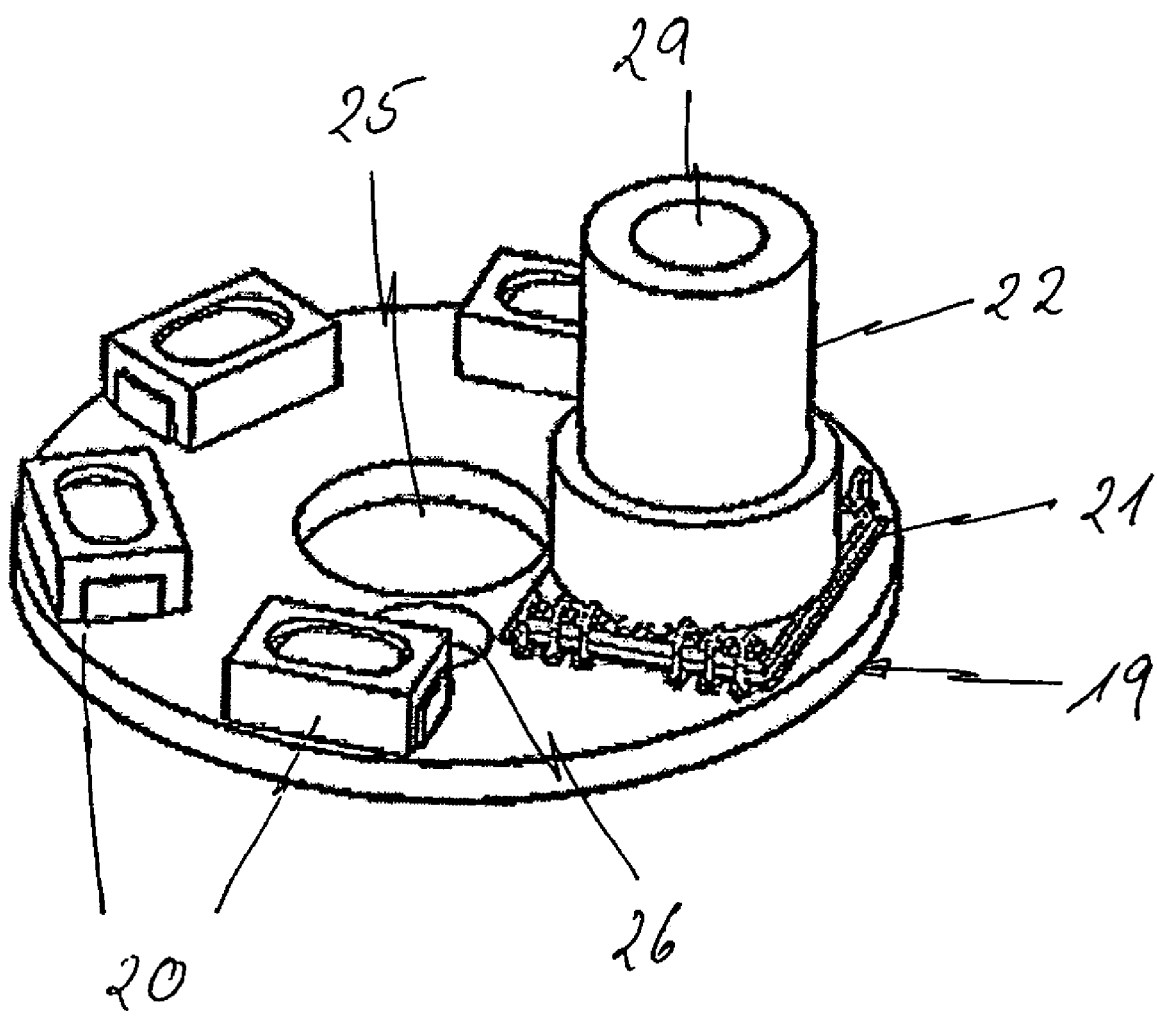
FIG. 5 shows a perspective view of a further embodiment of an endoscope shaft according to the invention.

In another embodiment of the invention according to FIG. 5, the lens retaining/holding element 22 can also be merely a cylindrical element disposed above the sensor 21 without receiving the working passage and the rinsing tube. In this embodiment the working passage and the rinsing tube are rather guided to the protective sheathing in parallel to the lens retaining/holding element and end there.

Finally, the retaining/holding element 22 may additionally be equipped with a tiltable and/or rotatable mirror and/or prism device projecting outwardly, i.e. beyond the protection cap, which is movable with respect to the chamber 29 receiving the optical/lens system, so that it optionally deflects light rays lying outside the normal area of incidence of the optical/lens system, provided in the chamber to the optical/lens system. In this way the angle of view of the optical/lens system can be optionally expanded to the side or even to the rear similarly to an adjustable rear view mirror.

The invention relates to an endoscope head which is equipped with a plurality of function-related units such as an optical/lens system, illuminating elements, rinsing nozzles and/or the like. The endoscope head substantially comprises a number of modular plug-in or click-in function-related supports 19, 22, 23 for receiving and/or forming appropriately allocated function-related units 20, 21, 38. It will be apparent to those skilled in the art that various modifications and variations can be made in the design and construction without departing from the scope or spirit of the invention.

We claim:

1. An endoscope head equipped with a plurality of function-related units comprising units including at least an optical system and illuminating element, wherein the endoscope head comprises a number of modular function-related supports that receive and/or form the function-related units, the endoscope head further comprising function-related supports including a plate-shaped support member for receiving electronic components, a retaining/holding element for an optical/lens system having at least one lens, a protection cap for covering the retaining/holding element and the support member, and a mounting adapter for attaching the endoscope head to an endoscope shaft, wherein the mounting adapter is adapted to provide and/or enable all connections between conduits and/or passages formed in the endoscope shaft and the function-related units of the endoscope head, and wherein the mounting adapter consists of two concentric coincident cylinder elements having different radii which are interconnected via an adapter plate which is formed on a front side of both cylinder elements such that a cavity in the form of a circle segment is formed between the cylinder elements which segment is divided into three sections by radial ribs, wherein the three sections comprise receiving means, respectively for receiving bending elements for bending the distal end portion of the endoscope relative to the endoscope shaft.

2. An endoscope head according to claim 1, wherein the function-related supports are adapted to correctly place or make operative the function-related units preferably automatically by assembling the function-related supports.

3. An endoscope head according to claim 2, wherein the function-related supports preferably have elastically deformable connecting portions adapted to be brought into predetermined engagement with each other for a snap and/or clamping connection.

4. An endoscope head according to claim 1, wherein on a first side facing the mounting adapter the function-related support has electrical contact surfaces adapted to be brought into contact with the electrical contact points of the mounting adapter when the function-related support is assembled with the mounting adapter, wherein electronic components arranged on a second side of the function-related support opposite to the electrical contact surfaces may be supplied with electric current by the electrical contact points via the electrical contact surfaces.

5. An endoscope head according to claim 4, wherein the retaining/holding element for the optical/lens system is attached to the first side of the function-related support on which is arranged the electronic components and which includes at least one chamber receiving the optical/lens system which is open toward a side of the retaining/holding element facing the protection cap and which is aligned with the function-related support above a camera chip provided in the function-related support when the function-related supports are assembled.

6. An endoscope head according to claim 1, wherein the material of the retaining/holding element is softer and/or more elastic than the material of the protection cap.

7. An endoscope head according to claim 5, wherein a tiltable and/or rotatable mirror and/or prism device which is movable with respect to the chamber receiving the optical/lens system to optionally deflect light rays outside the normal area of incidence of the optical/lens system is provided in the chamber to the optical/lens system.

8. A mounting adapter for an endoscope head according to claim 1, wherein the mounting adapter is adapted to form a mechanical connection between the endoscope head and an endoscope shaft, and to provide and/or ensure a connection between conduits and/or passages formed in the endoscope shaft and function-related units of the endoscope head.

9. A mounting adapter according to claim 8, wherein the mounting adapter comprises an outer substantially cylindrical sleeve and a coaxial inner substantially cylindrical sleeve which is connected preferably integrally with outer sleeve through profiled radial bracings, wherein the radial bracings provide and/or ensure at least partly, connection of conduits and/or passages with the function-related units.

10. A mounting adapter according to claim 9, wherein a mounting plate is formed on a first side of the mounting adapter to which the endoscope head is mountable, and wherein the mounting plate comprises mechanical and electrical connectors to form connections with the endoscope head.

11. A mounting adapter according to claim 10, wherein the electrical connectors of the mounting plate are provided as flexible contact arms formed in the mounting plate which further comprises electrical contact points projecting above the surface of the mounting plate.

12. An endoscope head equipped with a plurality of function-related units comprising units including at least an optical system and illuminating element, wherein the endoscope head comprises a number of modular function-related supports that receive and/or form the function-related units, the endoscope head further comprising function-related supports including a plate-shaped support member for receiving electronic components, a retaining/holding element for an optical/lens system having at least one lens, a protection cap for covering the retaining/holding element and the support member, and a mounting adapter for attaching the endoscope head to an endoscope shaft, wherein the mounting adapter is adapted to provide and/or enable all connections between conduits and/or passages formed in the endoscope shaft and the function-related units of the endoscope head, wherein the mounting adapter consists of two concentric coincident cylinder elements having different radii which are interconnected via an adapter plate which is formed on a front side of both cylinder elements such that a cavity in the form of a circle segment is formed between the cylinder elements which segment is divided into three sections by radial ribs, wherein the three sections comprise receiving means, respectively for receiving bending elements for bending the distal end portion of the endoscope relative to the endoscope shaft, wherein on a first side facing the mounting adapter the function-related support has electrical contact surfaces adapted to be brought into contact with the electrical contact points of the mounting adapter when the function-related support is assembled with the mounting adapter, wherein electronic components arranged on a second side of the function-related support opposite to the electrical contact surfaces may be supplied with electric current by the electrical contact points via the electrical contact surfaces, wherein the retaining/holding element for the optical/lens system is attached to the first side of the function-related support on which is arranged the electronic components and which includes at least one chamber receiving the optical/lens system which is open toward a side of the retaining/holding element facing the protection cap and which is aligned with the function-related support above a camera chip provided in the function-related support when the function-related supports are assembled, and wherein a tiltable and/or rotatable mirror and/or prism device which is movable with respect to the chamber receiving the optical/lens system to optionally deflect light rays outside the normal area of incidence of the optical/lens system is provided in the chamber to the optical/lens system.

\* \* \* \* \*